United States Patent
Horne, Jr.

(10) Patent No.: US 9,439,555 B2
(45) Date of Patent: Sep. 13, 2016

(54) LINER FOR ENDOSCOPE WORKING CHANNEL

(75) Inventor: Guy E. Horne, Jr., Dudley, MA (US)

(73) Assignee: Karl Storz Endovision, Inc., Charlton, MA (US)

(*) Notice: Subject to any disclaimer, the term of this patent is extended or adjusted under 35 U.S.C. 154(b) by 1667 days.

(21) Appl. No.: 11/436,144

(22) Filed: May 17, 2006

(65) Prior Publication Data

US 2006/0264708 A1 Nov. 23, 2006

Related U.S. Application Data

(60) Provisional application No. 60/682,897, filed on May 20, 2005.

(51) Int. Cl.
| A61B 1/00 | (2006.01) |
| A61B 1/04 | (2006.01) |
| A61B 1/018 | (2006.01) |
| G02B 23/24 | (2006.01) |
| A61B 1/012 | (2006.01) |

(52) U.S. Cl.
CPC ......... *A61B 1/00089* (2013.01); *A61B 1/0008* (2013.01); *A61B 1/018* (2013.01); *G02B 23/2476* (2013.01); *A61B 1/012* (2013.01)

(58) Field of Classification Search
USPC ............... 600/114, 127–130, 104, 106, 107, 600/121–125, 139–142, 153, 154; 604/523–527
See application file for complete search history.

(56) References Cited

U.S. PATENT DOCUMENTS

| 4,788,967 A * | 12/1988 | Ueda ............................. 600/129 |
| 4,872,458 A | 10/1989 | Kanehira et al. ............. 128/401 |
| 4,875,468 A * | 10/1989 | Krauter et al. ................ 600/153 |
| 4,918,521 A * | 4/1990 | Yabe et al. ....................... 348/76 |
| 4,967,732 A * | 11/1990 | Inoue ............................. 600/139 |
| 5,085,659 A | 2/1992 | Rydell ............................ 606/47 |
| 5,235,965 A | 8/1993 | Hiroya ............................. 128/6 |
| 5,608,831 A | 3/1997 | Pan ................................. 385/85 |
| 5,827,175 A | 10/1998 | Tanaka .......................... 600/104 |
| 5,941,815 A * | 8/1999 | Chang ........................... 600/114 |
| 6,063,084 A | 5/2000 | Farin .............................. 606/49 |
| 6,234,178 B1 | 5/2001 | Goble et al. ................... 128/898 |
| 6,547,721 B1 | 4/2003 | Higuma et al. ................ 600/133 |
| 6,773,392 B2 | 8/2004 | Kikuchi et al. ............... 600/109 |
| 6,780,180 B1 | 8/2004 | Goble et al. ................... 606/41 |
| 6,921,362 B2 * | 7/2005 | Ouchi ............................ 600/121 |
| 2002/0149858 A1 | 10/2002 | Anhalt ........................... 359/694 |

(Continued)

FOREIGN PATENT DOCUMENTS

| EP | 1 335 660 | 8/2003 |
| EP | 1723899 A1 | 11/2006 |
| JP | 59025724 A | 2/1984 |
| JP | 4012727 A | 1/1992 |

(Continued)

OTHER PUBLICATIONS

European Search Report; Sep. 26, 2006; 9 pages.

*Primary Examiner* — Ryan Henderson
(74) *Attorney, Agent, or Firm* — Whitmyer IP Group LLC

(57) ABSTRACT

A flexible endoscope insertion tube having at least one working channel extending in the axial direction of the flexible tube. One or more liners are in coaxial alignment with the distal end working channel of the tube. At least one ceramic tip liner may be disposed on the interior distal end of the endoscope working channel which protects the working channel from operational wear and tear.

24 Claims, 4 Drawing Sheets

(56) References Cited

U.S. PATENT DOCUMENTS

| | | | |
|---|---|---|---|
| 2003/0093073 A1 | 5/2003 | Platt | 606/49 |
| 2003/0097126 A1 | 5/2003 | Woloszko et al. | 606/41 |
| 2003/0130575 A1 | 7/2003 | Desai | 600/417 |
| 2004/0126071 A1 | 7/2004 | Henze et al. | 385/115 |
| 2004/0199226 A1 | 10/2004 | Shadduck | 607/96 |

FOREIGN PATENT DOCUMENTS

| | | |
|---|---|---|
| JP | 9108172 A | 4/1997 |
| JP | 2002301088 A | 10/2002 |
| JP | 2004016309 A | 1/2004 |
| WO | WO 2005/037087 | 4/2005 |

\* cited by examiner

LINER FOR ENDOSCOPE WORKING CHANNEL

CROSS-REFERENCE TO RELATED APPLICATIONS

This patent application claims the benefit of, under Title 35, United States Code, Section 119(e), U.S. Provisional Patent Application No. 60/682,897, filed May 20, 2005.

FIELD OF THE INVENTION

The present invention relates generally to flexible medical devices, and more particularly to flexible-type endoscopic devices which employ one or more liners for protecting working channels from wear and tear during usage.

BACKGROUND OF THE INVENTION

Generally, an endoscope is a medical device for insertion into a body passageway or cavity that enables an operator, positioned at a remote external location, to view and/or perform certain surgical procedures at a site internal to the patient's body. As is known, endoscopes may be either rigid or flexible, the later type providing either active or passive deflection of at least a portion thereof to facilitate reaching the internal site of interest. In general, a flexible endoscope includes a long flexible tubular member equipped with, for example, a miniature viewing device, an illumination device, and/or one or more working channels. The endoscope has a proximal end that remains external to the patient and a distal end having an endoscope tip for insertion into a body cavity of the patient.

Passive flexible endoscopes simply allow for the tubular member to deflect as it is inserted into various portions of the body (typically following the pathway of an elongated organ or cavity). Active flexible endoscopes on the other hand, allow the user to manipulate controls (typically at the proximal end of the endoscope) to cause at least a portion of the endoscope (typically the distal end) to deflect or flex in one or more directions. It is these flexible endoscopes with which the present invention is most concerned.

In certain known devices, the tubular member comprises a synthetic resin, such as polyurethane resin or ethylene tetrafluoride resin. A problem exists with the soft tubular members in that the soft material is susceptible to damage under normal operating conditions. For example, when resin is exposed at the distal end portion of the insertion section, and a laser probe is passed through one of the channels, the laser beam energy radiated from the distal end of the insertion section may burn the distal end of the tube either directly or indirectly by reflections of the beam energy from an irradiated region of a subject's body. This can result in a loss of structural integrity at the distal end tip of the endoscope.

In prior art devices, such as U.S. Pat. No. 4,788,967 to Ueda, the insertion section of an endoscope has a plurality of insertion channels extending in the axial direction of the flexible tube. A rigid member is attached to the distal end of the tube. The rigid member has through holes communicating with the channels, respectively. However, designs incorporating such rigid members are only useful where the rigid member replaces a distal end portion of the flexible endoscope tube in order to communicate with the various channels. This may lead to manufacturing difficulties including the step of modifying the distal end portion to accept the rigid member, as well as the addition of a bulky rigid member. This results in an unnecessarily heavy ended insertion tube.

U.S. Pat. No. 5,085,659 to Rydell relates to a biopsy instrument comprises an elongated flexible tube having a sharpened metal sleeve affixed to its distal end. The sleeve may be connected to the tube using a ceramic plug. However, this design creates a metallic edge outside of the flexible tube channel, thus does not protect the inner surface of the working channel from normal wear and tear. Moreover, the ceramic plug occludes the biopsy channel limiting a surgeon's ability to place tools therein.

U.S. Pat. No. 4,872,458 to Kanehira et al. relates to a thermotherapy apparatus used for performing a thermotherapy for a diseased part of a tumor such as a cancer of a living body. A heating portion is arranged in a distal end portion at the body cavity side of a probe which can be inserted in the body cavity through an endoscope or the like or a distal end portion at the body cavity side of an insertion portion of the endoscope. The heating portion has a far-infrared radiation ceramic member, and a heater for heating the far-infrared radiation ceramic member. However, this design does not protect the interior portion of a working channel from wear and tear.

What is desired, therefore, is a durable working channel in a flexible endoscope the use of which does not result in a loss of deflection at the distal end tip of the endoscope, which does not break down easily under normal wear and tear conditions, which has high resilience, and which does not fatigue and permanently deform, thereby shortening the life of the endoscope.

SUMMARY OF THE INVENTION

It is the object of the present invention to protect the working channels of the flexible tubular member of an endoscope.

It is the object of the present invention not to reduce deflection at the distal end tip of a flexible endoscope.

It is the object of the present invention to provide an endoscope insertion tube that does not break down easily under normal wear and tear conditions.

It is the object of the present invention to make an endoscope working channel that is less susceptible to damage caused by contact with laser light energy.

It is the object of the present invention to provide a protective sleeve which is easily sized to a working channel.

These and other objectives of the present invention are met by providing a medical device comprising an insertion tube having a proximal end and a distal end, and at least one working channel having an inner surface, the working channel extending from the proximal end to the distal end in an axial direction of the tube; and a liner disposed upon the inner surface at the distal end of the working channel. Preferably the liner is a ceramic sleeve. The ceramic sleeve is made of material selected from the group consisting of mullite, fused silica, alumina, and combinations thereof. Optionally, the liner is made of material selected from the group consisting of metal, alloy, ceramic, glass, glass-ceramic, polymeric material, composite, coatings, adhesives, thermoplastic and combinations thereof. The liner may be tube shaped sleeve having a distal opening adjacent to the distal end of the insertion tube, and a proximal opening opposite the distal opening, wherein the distal opening and proximal opening are connected by a passage. The passage has a central axis coaxial to the working channel. The liner has a first length along the outside of the liner and a second length along the inside of the liner, the first length substantially equal to the second length, and at least one edge which is substantially perpendicular to the first length and the second length. The liner may have a first length along the outside of the liner and a second length along the inside of the liner, the first length longer than the second length to form a first beveled edge adjacent to the distal opening and a second beveled edge adjacent to the proximal opening. The first beveled edge may have an angle of approximately 45 degrees. The second beveled edge may have an angle of approximately 45 degrees. The working channel of the endoscope may have a distal end opening, and the liner is disposed in the working channel immediately adjacent to the distal end opening. The insertion tube may be formed of a bendable resin. Preferably the liner is a tube. The liner may optionally have a beveled distal edge, however this configuration is less preferred. The liner has a first length, a first width, a first height, and a first thickness. The first length of the liner is between about 1.0 mm and 3.0 mm. Preferably, in the case of a ureteroscope, the first length is approximately 2.5 mm.

The objects of the present invention are further met by providing a medical device comprising an insertion tube having a proximal end and a distal end, and at least one working channel having an inner surface extending from the proximal end to the distal end in an axial direction of the tube; and a ceramic liner having a proximal end and a distal end disposed upon the inner surface within the distal end of the working channel, wherein the liner comprises a distal opening adjacent to the distal end of the working channel and a proximal opening opposite the distal opening and a passage between the distal opening and the proximal opening in coaxial alignment with the working channel. The insertion tube is preferably a flexible endoscope tube. Preferably, the ceramic liner has a first length along the outside of the liner and a second length along the inside of the liner, and at least one edge between the first length and the second length. The at least one edge may be beveled and have an angle of approximately 45 degrees. The at least one edge comprises a first edge and a second edge characterized as beveled and having two angles of inclination of approximately 45 degrees.

The objects of the present invention are met by providing a medical device comprising a distal end plate disposed upon the distal end of the insertion tube. The distal end plate has a bore in coaxial alignment with the working channel of the insertion tube. The liner is placed within the bore, disposed upon the inner wall thereof. The distal end plate is made out of metal such as stainless steel and affixed to the distal end of the insertion tube. The liner inside the distal end plate is preferably made of ceramic material.

The objectives of the present invention are further met by providing a method of sealing a working channel of a flexible endoscope tube comprising: depositing a liner upon the inner surface of a working channel at the distal end of the working channel; and binding the liner to the inner wall of the working channel immediately adjacent to the distal end of the endoscope tube. The method further comprises the step of assembling a liner made of material selected from the group consisting of metal, alloy, ceramic, glass, glass-ceramic, polymeric material, composite, coatings, adhesives, thermoplastic and combinations thereof. The method may further include using ceramic material selected from the group consisting of mullite, fused silica, alumina, and combinations thereof.

DETAILED DESCRIPTION OF THE DRAWINGS

Figure 1:
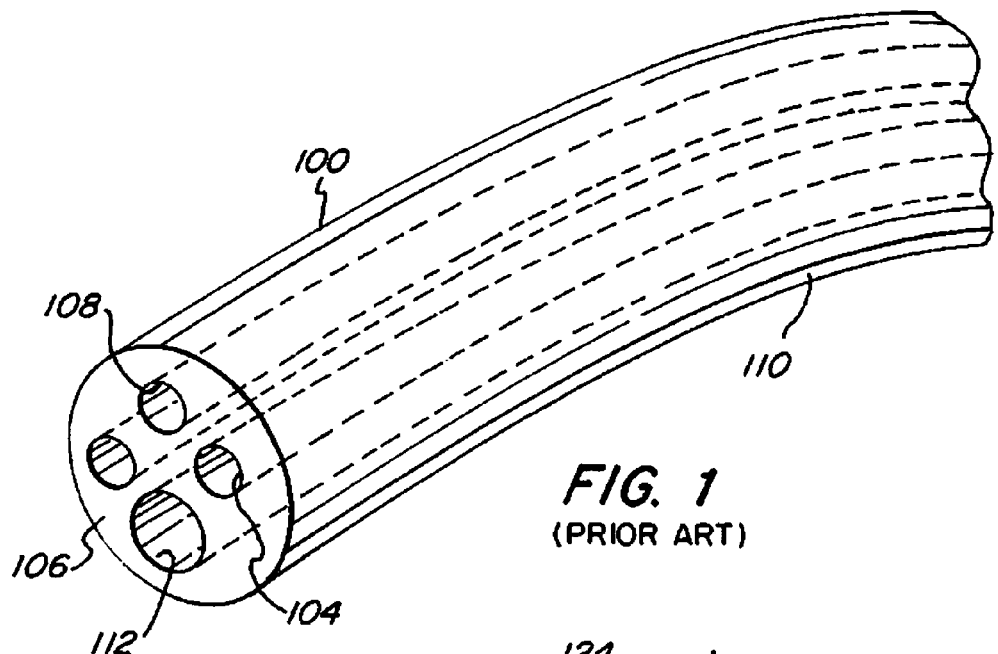
FIG. 1 is an isometric view, partially in phantom, of a prior art flexible endoscope.

A typical flexible endoscope 100 is illustrated in FIG. 1. An illumination device of endoscope 100 typically includes a lens 104 at an endoscope tip 106. Lens 104 is positioned proximate to a viewing device 108. Light emanates from lens 104 to enable viewing device 108 to capture images in the body cavity and electrically or optically transmit the images through a tubular body 110 of endoscope 100 for display at an external monitor. Once viewing the transmitted images, the endoscope operator may insert one or more surgical instruments through one or more working channels 112 to perform an endoscopic procedure at the internal body cavity site. These endoscopic procedures may include, for example, snare resections, injections, or biopsies of particular internal areas of the patient's body. Alternately, endoscope 100 may be used simply for viewing.

Referring now to FIG. 2, an isometric view of liner 120 is illustrated. Liner 120 is designed to be inserted into working channel 112 of an endoscope to prevent laser damage at the distal end tip of the endoscope, and prevent fatigue and breakdown of the tip of the endoscope. Liner 120 generally increases the working life of an endoscope by protecting the distal tip of the endoscope's working channel 112. Liner 120 has a longitudinal central axis A-A' extending through distal opening 122, and proximal opening 124. Liner 120 may be of any predetermined shape and size, however is preferably a cylindrical or tubular shape which aligns with and is disposed upon the interior portion of the endoscope working channel 112 to which it will be inserted. Liner 120 has a predetermined first length 126 extending from distal opening 122 to proximal opening 124. For some embodiments, first length 126 is preferably between about 0.5 mm to about 10 mm, more preferably about 2.5 mm. Liner 120 has a predetermined first width 128. For some embodiments, first width 128 is preferably between about 0.5 mm to about 10 mm, more preferably about 2.5 mm. For some embodiments, first height 130 is preferably between about 0.5 mm to about 10 mm, more preferably about 2.5 mm. For some embodiments, first thickness is preferably between about 0.25 mm to about 3 mm, more preferably about 1.2 mm.

All dimensions, including first length, width, height and thickness are predetermined in order to fit a corresponding preselected endoscope working channel. For example, the dimension of the liner may be predetermined to be sized to fit into the distal end tip of a working channel for a Karl Storz® ureteroscope, such as a preselected flexible standard 7.5 distal end ureteroscope. Moreover, a working channel may be modified to accommodate a liner, for example by changing the dimensions of the bore. First thickness is selected to ensure that the endoscope tube is substantially covered while distal opening 122 remains wide enough for a surgeon to fit surgical instruments there through. One of ordinary skill in the art recognizes that the liner can be easily sized to larger and smaller working channels for the same or different endoscope insertion tubes, and that the thickness of liner 120 may be modified so long as the working channel does not become occluded.

Liner 120 may be made out of any material that one of ordinary skill in the art would use to make a liner for surgical tubing which may be introduced into a patients body, including but not limited to metals, alloys, ceramics, glasses, and glass-ceramics, polymeric materials, composites, coatings, adhesives, and thermoplastics. Ceramic material is preferred as it has specific properties that insulate against laser energy damage. Ceramic materials include nonmetallic, inorganic compounds that exhibit great strength and stiffness, resistance to corrosion and wear, and have a low density, such as for example, mullite, fused silica or alumina. Alternatively, the liner may be metallic. However, ceramic liners are preferred for they advantageously have, among other characteristics, a high ability to withstand steep temperature gradients and large thermal shocks, good machinability, high bonding capability, and ease of providing a seal between the endoscope tube and the edge of the ceramic liner. It has also been found that ceramic material is preferred over metallic material because it can withstand higher energy levels than some metals. For example, stainless steel endtips are damaged by energy levels of 0.8 Joules, while ceramic endtips or liners have been found to withstand energy levels in excess of 2.5 Joules.

Figure 2A:
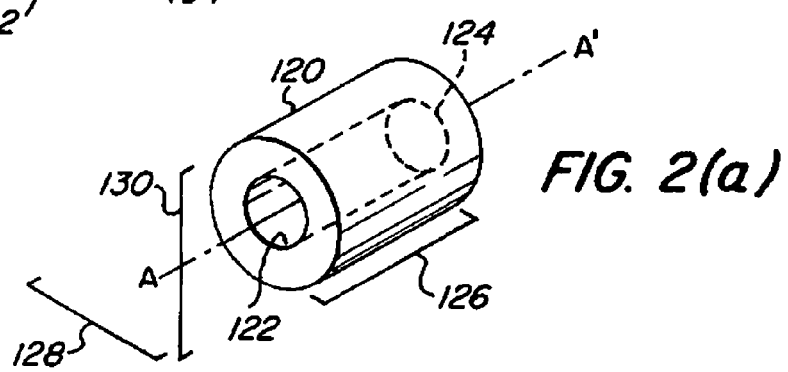
FIG. 2(a) is an isometric view of a liner of the present invention.
Figure 2B:
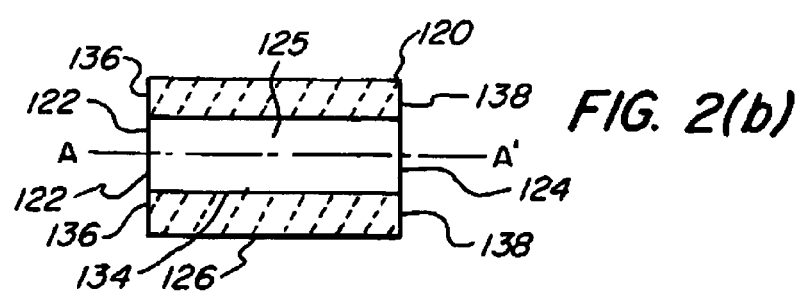
FIG. 2(b) is a cross-sectional side view of the embodiment of FIG. 2(a).

Referring now to FIG. 2(b), a cross-sectional side view of the embodiment of FIG. 2(a) is illustrated. In this embodiment first length 126 along the outside edge of liner 120 is substantially equal to second length 134 along the inside edge of liner 120. Such a configuration creates first edge 136 which is substantially perpendicular to first length 126 and second length 134. When liner 120 is in a substantially cylindrical shape, first edge 136 extends around liner in a circular manner. Second edge 138 is similarly positioned around distal opening 124. Passage 125 extends from distal opening 122 to proximal opening 124.

Figure 3:
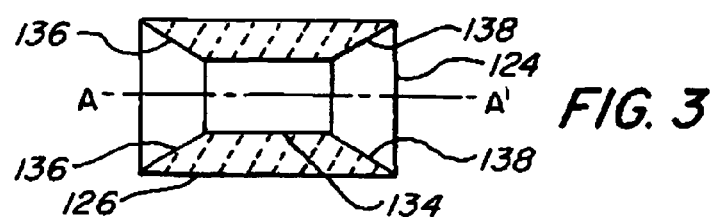
FIG. 3 is a cross-sectional side view of another embodiment of the liner shown in FIG. 2(a).

Referring now to FIG. 3, an isomeric cross-sectional side view of another embodiment of liner 120 is shown along axis A-A'. Here, first length 126 is longer than second length 134 such that first edge 136 is beveled. Beveled first edge 136 maximizes the size of distal opening 122 so that liner 120 does not limit a surgeon's ability to place a tool near or outside distal opening 122 in a patient's body. Beveled first edge is of a predetermined length such as 0.15 mm for a ureteroscope. First length 126 and second length 134 are preselected such that first edge 136 forms an angle between 5 to 50 degrees, preferably about 45 degrees. Second edge 138 may be beveled such that its angle of inclination is equal to that of first edge 136. Here, second edge 136 angles at approximately 45 degrees to facilitate the entry of a surgeon's tool (not shown in FIG. 2(b)) into the liner, and minimize the possibility that a surgeon's tool will snag on liner 120 near proximal opening 124.

Figure 4:
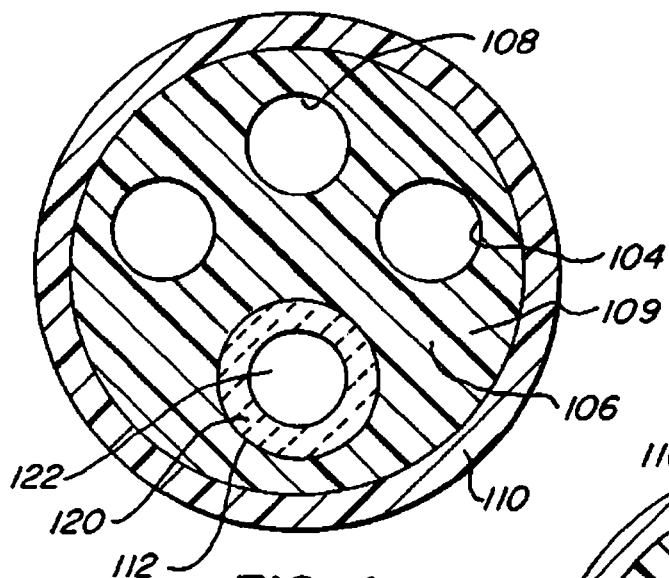
FIG. 4 is a view of the distal end of a flexible endoscope with liner of FIG. 2.

Referring now to FIG. 4 a front view of a flexible endoscope with liner of FIG. 2 is shown. Flexible endoscope 100 includes one or more working channels 112 at an endoscope tip 106. Lens 104 is positioned proximate to a viewing device 108. Light emanates from lens 104 to enable viewing device 108 to capture images in the body cavity and electrically or optically transmit the images through a tubular body 110 of endoscope 100 for display at an external monitor. Once viewing the transmitted images, the endoscope operator may insert one or more surgical instruments through one or more working channels 112 to perform an endoscopic procedure at the internal body cavity site. Liner 120 is positioned inside working channel 112, such that it is disposed upon the working channel wall immediately adjacent to distal opening 122. Preferably, liner 120 is a ceramic sleeve bonded to working channel 112 with an adhesive. In one preferred embodiment, the surface of distal end tip 106 and front surface of liner 120 are flush, such that the distal edges of end tip 106 and liner 120 form a uniform flat surface 109.

Figure 5:
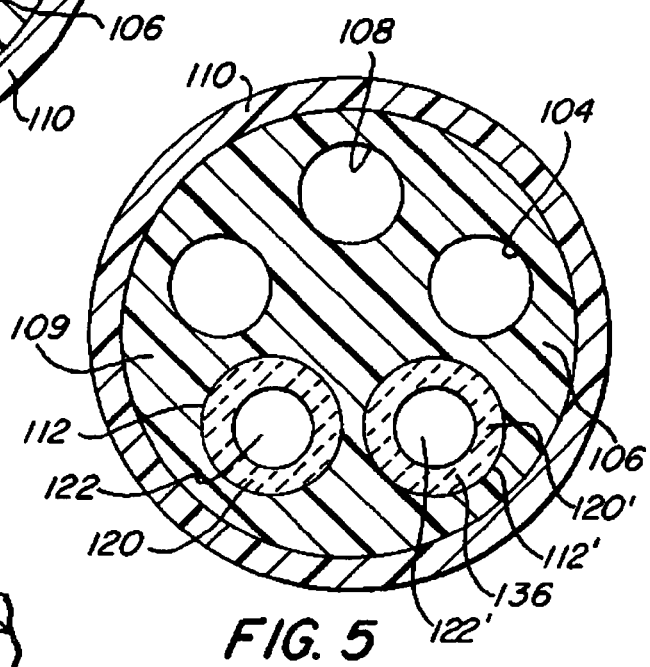
FIG. 5 is a front isometric view of the distal end of a flexible endoscope of the present invention with more than one liner of FIG. 2.

Referring now to FIG. 5, a front view of a flexible endoscope with liner of FIG. 2 is shown. Flexible endoscope 100 includes more than one working channels 112 at an endoscope tip 106. Lens 104 is positioned proximate to a viewing device 108. Light emanates from lens 104 to enable viewing device 108 to capture images in the body cavity and electrically or optically transmit the images through a tubular body 110 of endoscope 100 for display at an external monitor. Liner 120 is positioned inside working channel 112, such that it is disposed upon the working channel wall immediately adjacent to distal opening 122. Liner 120' is positioned inside working channel 112', such that it is disposed upon the working channel wall immediately adjacent to distal opening 122'. Preferably, liner 120 and 120' are ceramic sleeves bonded to working channel 112 with an adhesive. In one preferred embodiment, the surface of distal end tip 106 and front surface of liners 120 and 120' are flush, such that the distal edges of end tip 106 and liners 120 and 120' form a uniform flat surface 109. Optionally, working channels 112 and 112' may be different in that working channel 112 is larger than working channel 112'. Liners 120 and 120' may be the same or different predetermined sizes, and modified to fit variable size working channels in different types of endoscopes. Liner 120' may optionally be of the type shown in FIG. 3, where a first edge 136 and second edge 138 (not shown in FIG. 5) are beveled.

Figure 6:
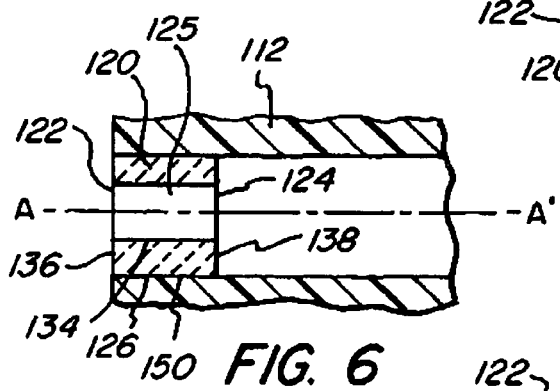
FIG. 6 is a cross section of the working channel of FIG. 4.

Referring now to FIG. 6, a cross section of the working channel of FIG. 4 is shown. Tubular liner 120 is disposed upon working channel 112 such the liner is in coaxial alignment with the working channel along axis A-A'. First length 126 along the outside edge of liner 120 is substantially equal to second length 134 along the inside edge 150 of liner 120. This configuration creates first edge 136 which is substantially perpendicular to first length 126 and second length 134. When liner 120 is in a substantially cylindrical shape, first edge 136 extends around liner in a circular manner. Second edge 138 is similarly positioned around distal opening 124. Passage 125 extends from distal opening 122 to proximal opening 124.

Figure 7:
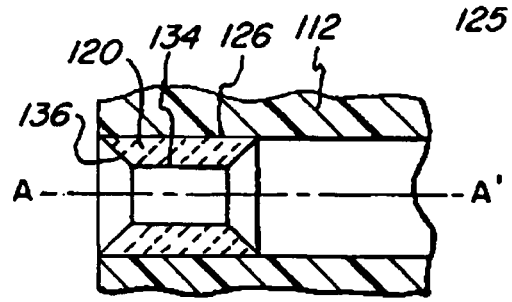
FIG. 7 is a cross section of the working channel with liner of FIG. 3.

Referring now to FIG. 7, a cross section of the working channel with liner of FIG. 3 is shown. Liner 120 is disposed upon working channel 112 such the liner is in coaxial alignment with the working channel along axis A-A'. Here, first length 126 is longer than second length 134 such that first edge 136 is beveled. Beveled first edge 136 maximizes the size of distal opening 122 so that liner 120 does not limit a surgeon's ability to place a tool near or outside distal opening 122 in a patient's body. Beveled first edge is of a predetermined length such as between about 0.1 mm to about 2 cm preferably about 0.15 mm for a ureteroscope. First length 126 and second length 134 are preselected such that first edge 136 forms an angle between 5 to 50 degrees preferably about 45 degrees.

Figure 8:
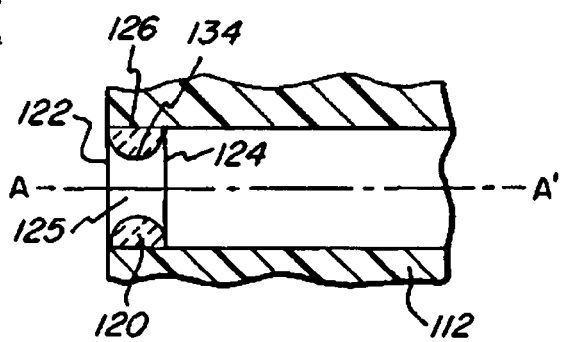
FIG. 8 is a cross section of an endoscope working channel with another liner.

Referring now to FIG. 8 is a cross section of an endoscope working channel with another liner is shown. Liner 120 is disposed upon working channel 112 such the liner is in coaxial alignment with the working channel along axis A-A'. First length 126 along the outside edge of liner 120 is shorter than second length 134 along the inside edge of liner 120. This configuration creates an arc shaped configuration which prevents a surgeon's tool from snagging on liner 120. Passage 125 extends from distal opening 122 to proximal opening 124.

Figure 9:
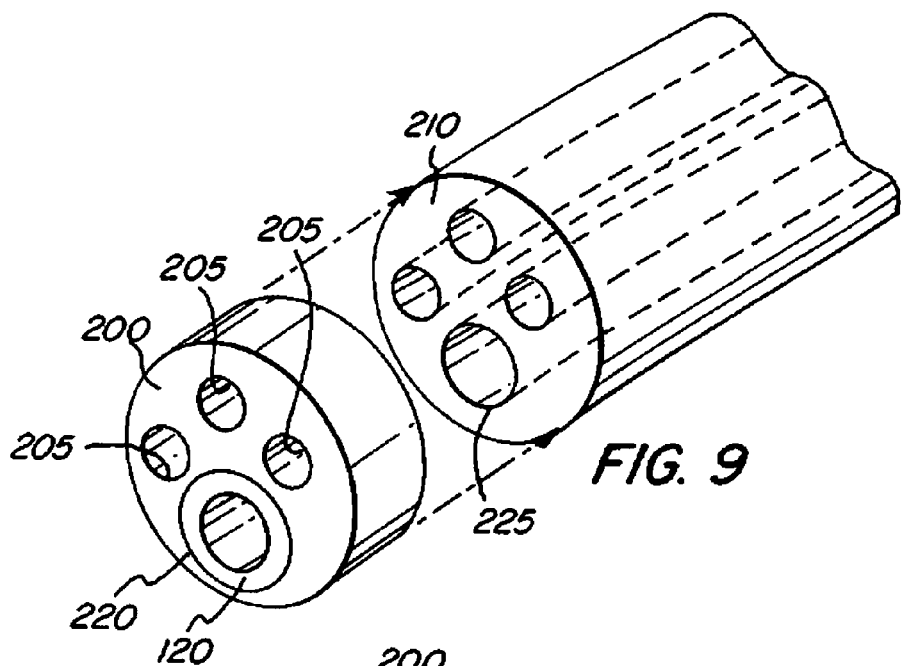
FIG. 9 is an exploded view of another embodiment of the present invention with distal end plate.

Referring now to FIG. 9, a front exploded view of another embodiment of the present invention is shown. Here, distal end plate 200 is configured to connect to the distal end 210 of flexible endoscope. Although the flexible endoscope is shown as a multilumen design, the present invention is equally applicable to a single lumen configuration. Distal end plate 200 may be made out of any suitable material for use with an endoscope such as plastic, metal, or stainless steel. Distal end plate 200 is of a predetermined shape such that it does not obstruct or hinder the operation of the flexible endoscope components. Here distal end plate 200 is shown having apertures 205 designed to be in coaxial alignment with the nonworking channels of the endoscope tubing. Optionally, distal end plate 200 may be configured solely to surround the working channel thus leaving distal end face 210 substantially uncovered. Distal end plate 200 further comprises a working channel bore 220 coaxial alignment with working channel 225 of the flexible endoscope. Working channel bore 220 has an inner wall and liner 120 disposed thereon. Liner 120 is of a predetermined shape and size, preferably having a central opening that is the same size as the working channel 225. Liner 120 is fixedly attached to the distal end plate 200 using an adhesive or any means known in the art to fixedly attach a liner to a plate.

Figure 10:
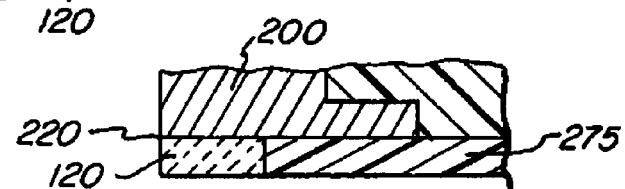
FIG. 10 is a cross section of the working channel of another preferred embodiment with distal end plate.
Figure 10:
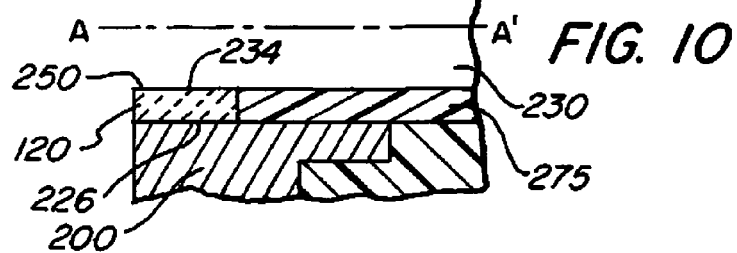

Referring now to FIG. 10 a cross section of the working channel of another preferred embodiment is shown. Liner 120 is disposed upon central bore 220 of distal end plate 200 such that liner 120 is in coaxial alignment with the working channel 230 along axis A-A'. First length 226 along the outside edge of liner 120 is substantially equal to second length 234 along the inside edge 250 of liner 120. This configuration creates first edge 236 which is substantially perpendicular to first length 226 and second length 234. When liner 120 is in a substantially cylindrical shape, first edge 236 extends around liner in a circular manner. Soft channel tube 275 is positioned adjacent to liner 120.

Figure 11:
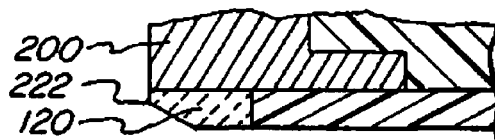
FIG. 11 is a cross section of the working channel of another preferred embodiment with distal end plate.
Figure 11:
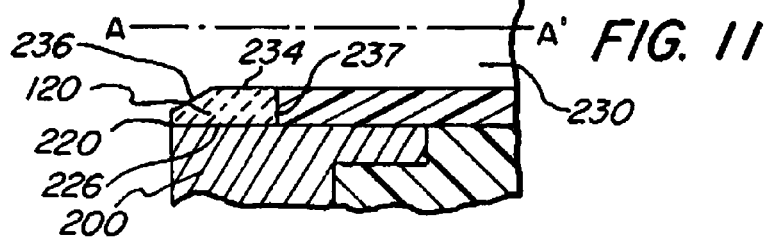

Referring now to FIG. 11 a cross section of the working channel of another preferred embodiment is shown. Liner 120 is disposed upon central bore 220 of distal end plate 200 such that liner 120 is in coaxial alignment with the working channel 230 along axis A-A'. Here, first length 226 is longer than second length 234 such that first edge 236 is beveled. Beveled first edge 236 maximizes the size of distal opening 222 so that liner 120 does not limit a surgeon's ability to place a tool near or outside distal opening 222 in a patient's body. Beveled first edge is of a predetermined length such as between about 0.1 mm to about 2 cm preferably about 0.15 mm for a ureteroscope. First length 226 and second length 234 are preselected such that first edge 236 forms an angle between 5 to 50 degrees preferably about 45 degrees. Second edge 237 is not beveled to promote even alignment between the distal end plate 200 and distal end of flexible endoscope tubing.

Figure 12:
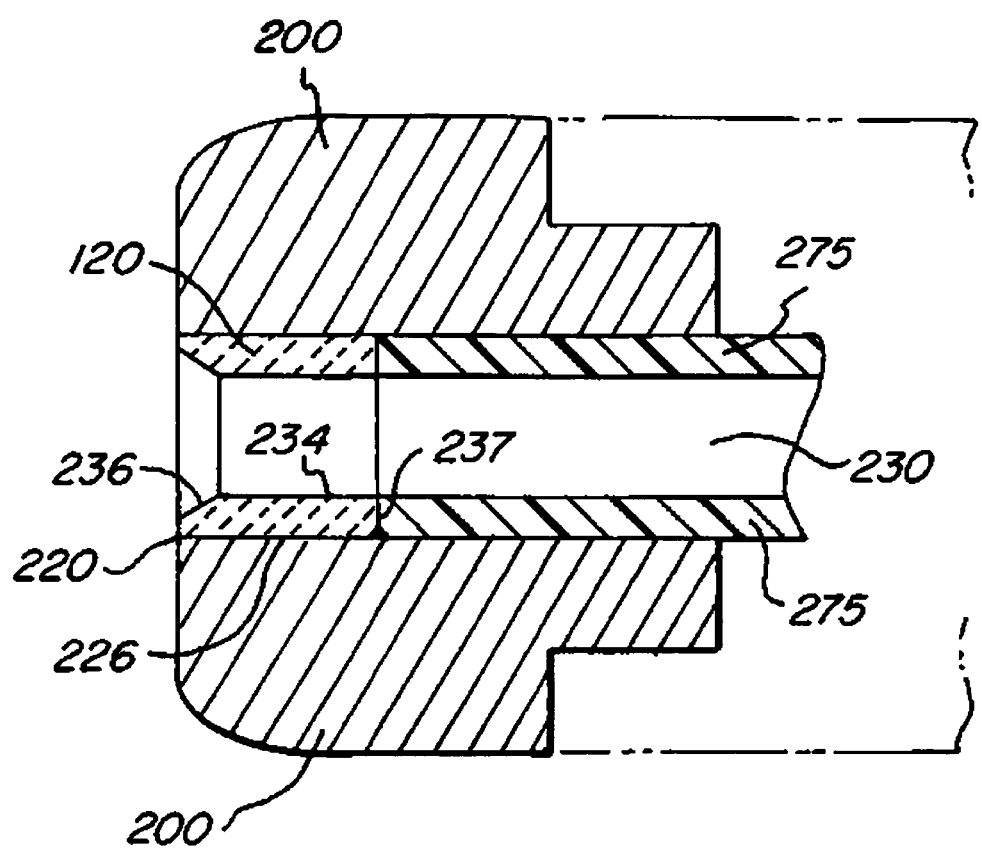
FIG. 12 is a cross sectional view of another embodiment of the present invention.

Referring now to FIG. 12 a cross section of another embodiment of the present invention is shown. Liner 120 is disposed upon central bore 220 of distal end plate 200 such that liner 120 is in coaxial alignment with the working channel 230. Beveled first edge 236 maximizes the size of distal opening so that liner 120 does not limit a surgeon's ability to place a tool near or outside distal opening in a patient's body. Beveled first edge is of a predetermined length such as between about 0.1 mm to about 2 cm preferably about 0.15 mm for a ureteroscope. First length 226 and second length 234 are preselected such that first edge 236 forms an angle between 5 to 50 degrees preferably about 45 degrees. Second edge 237 is not beveled to promote even alignment between liner 120 and channel tube 275. Distal end plate 200 is made out of metal and surrounds liner 120 as well as the distal end of channel tube 275. Distal end plate 200, liner 120, and channel tube 275 are fixed into place using an adhesive or any suitable means for fixedly connecting components of a medical device known in the art.

The invention also relates to a method of making such liners which include the steps of selecting a liner material, forming at least one liner, depositing the material within the working channel, and binding the liner to the working channel, or bore of distal end plate. Materials for making the liner are selected from metal, alloy, ceramic, glass, glass-ceramic, polymeric material, composite, coatings, adhesives, thermoplastic and combinations thereof, preferably ceramic material such as metal, alloy, ceramic, glass, glass-ceramic, polymeric material, composite, coatings, adhesives, thermoplastic and combinations thereof. The liner is formed using methods available to one of ordinary skill in the art. Adhesives suitable for use in a medical device for insertion into a patient's body are used for binding liner 120 to the working channel 112.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:
1. An endoscope, comprising:
an insertion tube having a proximal end and a distal end, and at least one working channel located within the insertion tube, the working channel having an inner surface and extending from the proximal end to the distal end in an axial direction of the insertion tube;
a distal end plate disposed upon the distal end of the insertion tube, the distal end plate having a bore in coaxial alignment with the working channel;
a liner in coaxial alignment with the distal end of the working channel, the liner being formed from a ceramic material and being disposed within the bore of the distal end plate; and
a channel tube disposed within the inner surface of the working channel and partially within the bore of the distal end plate, such that the channel tube and liner are adjacent to one another, wherein an inner surface of the channel tube and an inner surface of the liner are flush to form a constant diameter within the working channel.

2. The endoscope of claim 1, wherein the liner is a ceramic sleeve.

3. The endoscope of claim 2, wherein the ceramic sleeve is made of material selected from the group consisting of mullite, fused silica, alumina, and combinations thereof.

4. The endoscope of claim 1, wherein the liner is made of material selected from the group consisting of metal, alloy, ceramic, glass, glass-ceramic, polymeric material, composite, coatings, adhesives, thermoplastic and combinations thereof.

5. The endoscope of claim 1, wherein the liner is a tube shaped sleeve having a distal opening adjacent to the distal end of the insertion tube, and a proximal opening opposite the distal opening, wherein the distal opening and proximal opening are connected by a passage.

6. The endoscope of claim 5, wherein the passage has a central axis coaxial to the working channel.

7. The endoscope of claim 1, wherein the liner has a first length along the outside of the liner and a second length along the inside of the liner, the first length substantially equal to the second length, and at least one edge which is substantially perpendicular to the first length and the second length.

8. The endoscope of claim 1, wherein the liner has a first length along an outside of the liner and a second length along an inside of the liner, the first length longer than the second length to form a first beveled edge adjacent to a distal opening.

9. The endoscope of claim 8, wherein the first beveled edge has an angle of approximately 45 degrees.

10. The endoscope of claim 1, wherein the insertion tube is formed of a bendable resin.

11. The endoscope of claim 1, wherein the liner is a tube.

12. The endoscope of claim 1, wherein the liner has a first length, a first width, a first height, and a first thickness.

13. The endoscope of claim 12, wherein the first length of the liner is between about 1.0 mm and 3.0 mm.

14. The endoscope of claim 12, wherein the first length of said liner is approximately 2.5 mm.

15. The endoscope of claim 1, wherein the insertion tube is flexible.

16. An endoscope, comprising:
an insertion tube having a proximal end and a distal end, and at least one working channel having an inner surface extending from the proximal end to the distal end in an axial direction of the tube, the working channel being located within the insertion tube;
a distal end plate disposed upon the distal end of the insertion tube, the distal end plate having a bore in coaxial alignment with the working channel;
a ceramic liner having a proximal end and a distal end disposed within the bore of the distal end plate, wherein the liner comprises a distal opening adjacent to the distal end of the working channel and a proximal opening opposite the distal opening and a passage between the distal opening and the proximal opening in coaxial alignment with the working channel; and
a channel tube disposed within the inner surface of the working channel and partially within the bore of the distal end plate, wherein the channel tube is adjacently provided to the ceramic liner,
wherein an inner surface of the channel tube and an inner surface of the liner are flush to form a constant diameter within the working channel.

17. The endoscope of claim 16, wherein the insertion tube is a flexible endoscope tube.

18. The endoscope of claim 16, wherein the ceramic liner has a first length along an outside of the liner and a second length along an inside of the liner, and one edge between the first length and the second length at the distal end of the working channel.

19. The endoscope of claim 18, wherein the one edge is beveled and has an angle of approximately 45 degrees.

20. The endoscope of claim 16, further comprising a viewing device and a lens.

21. The endoscope of claim 16, wherein the insertion tube is flexible.

22. A method of making an endoscope, the method comprising:
providing an insertion tube having a proximal end and a distal end, and at least one working channel having an inner surface, the working channel extending from the proximal end to the distal end in an axial direction of the tube, the working channel being located within the insertion tube;
providing a distal end plate disposed upon the distal end of the insertion tube, the distal end plate having a bore in coaxial alignment with the working channel;
depositing a channel tube within the inner surface of the working channel at the distal end of the working channel, such that the channel tube is partially within the bore of the distal end plate;
disposing a ceramic liner in the bore of the distal end plate, such that the liner is adjacent to the channel tube, and such that an inner surface of the channel tube and an inner surface of the liner are flush to form a constant diameter within the working channel; and
binding the liner to a surface of the distal end plate that defines the bore.

23. The method of claim 22, further comprising the step of assembling a liner made of material selected from the group consisting of metal, alloy, ceramic, glass, glass-ceramic, polymeric material, composite, coatings, adhesives, thermoplastic and combinations thereof.

24. The method of claim 23, wherein the ceramic is material selected from the group consisting of mullite, fused silica, alumina, and combinations thereof.

* * * * *